(12) United States Patent
Burgass et al.

(10) Patent No.: US 6,223,588 B1
(45) Date of Patent: May 1, 2001

(54) DEW POINT AND BUBBLE POINT MEASUREMENT (75) Inventors: Rhoderick William Burgass; Adrian Christopher Todd; Sayed Ali Danesh; Bahman Tohidi Kalorazi, all of Edinburgh (GB)

(73) Assignee: Heriot-Watt University, Edinburgh (GB)

( * ) Notice: Subject to any disclaimer, the term of this patent is extended or adjusted under 35 U.S.C. 154(b) by 0 days.

(21) Appl. No.: 09/402,387
(22) PCT Filed: Apr. 8, 1998
(86) PCT No.: PCT/GB98/01004
§ 371 Date: Dec. 22, 1999
§ 102(e) Date: Dec. 22, 1999
(87) PCT Pub. No.: WO98/45691
PCT Pub. Date: Oct. 15, 1998

(30) Foreign Application Priority Data

Apr. 5, 1997 (GB) .................................................. 9706990

(51) Int. Cl.[7] .......................... G01N 25/68; G01N 11/00; E21B 47/06
(52) U.S. Cl. ........................ 73/53.01; 73/61.45; 73/61.47; 73/19.03; 73/19.01
(58) Field of Search ............................... 73/53.01, 61.45, 73/61.47, 61.78, 64.51, 19.03, 19.06, 19.08, 19.05, 19.1

(56) References Cited

U.S. PATENT DOCUMENTS

| 4,235,095 | * | 11/1980 | Liebermann | ............................... 73/19 |
|---|---|---|---|---|
| 4,378,168 | | 3/1983 | Kuisma | ................................... 374/28 |
| 4,607,520 | * | 8/1986 | Dam | ........................................... 73/19 |
| 4,727,277 | | 2/1988 | Adams | .................................... 310/321 |
| 4,730,493 | * | 3/1988 | Lebaud et al. | .......................... 73/599 |
| 4,944,191 | * | 7/1990 | Pastrone et al. | ........................ 73/599 |
| 5,051,645 | | 9/1991 | Brace et al. | ............................ 310/313 |
| 5,201,215 | | 4/1993 | Granstaff et al. | .................... 73/54.41 |
| 5,329,811 | * | 7/1994 | Schultz et al. | .......................... 73/155 |
| 5,394,732 | * | 3/1995 | Johnson et al. | ........................ 73/19.1 |
| 5,524,475 | * | 6/1996 | Kolpak et al. | ........................ 73/19.03 |
| 5,635,631 | * | 6/1997 | Yesudas et al. | ...................... 73/61.46 |
| 5,659,129 | * | 8/1997 | Asoyan et al. | ....................... 73/54.25 |

FOREIGN PATENT DOCUMENTS 2 737 780 A1   11/1995   (FR) .
WO 83/01989    6/1983    (WO) .

OTHER PUBLICATIONS

Amyx, J.W.; Bass Jr., D. and Whiting, R. Petroleum Reservoir Engineering (Physical Properties) McGraw–Hill, pp. 220–229, 1960.*

* cited by examiner

Primary Examiner—Hezron Williams
Assistant Examiner—David J. Wiggins
(74) Attorney, Agent, or Firm—Wolf, Greenfield & Sacks, P.C.

(57) ABSTRACT

Apparatus and method for detecting the dew point or bubble point phase transition in fluid. The apparatus used comprises a piezoelectric crystal sensor and a signal analyser. The phase transition of the fluid is measured by monitoring, directly or indirectly, change in the resonant frequency of the piezoelectric crystal sensor while said one of the temperature and pressure is varied, so as to detect a substantial change in said resonant frequency and/or in the rate of change in resonant frequency with change in the varying one of the temperature and pressure.

30 Claims, 5 Drawing Sheets

DEW POINT AND BUBBLE POINT MEASUREMENT

The present invention relates to methods and apparatus for detecting and/or measuring dew point (DP) or bubble point (BP) temperatures and/or pressures, and particularly, but not exclusively, for measuring the dew point or bubble point temperatures and/or pressures of hydrocarbon mixtures.

The dew point (DP) or bubble point (BP) is the point (in terms of pressure and temperature) at which, in a single phase (liquid or gas) fluid, a phase transition, (i.e. liquid to gas, or gas to liquid) occurs. The DP or BP of a fluid is an important indicator for determining the properties and/or composition of a fluid sample, and thus also its likely behaviour under certain conditions. For this reason it is important to be able to measure the DP or BP of a fluid, in many applications. One application is in relation to natural oil reservoirs where it is often desirable to be able to measure the DP or BP of a hydrocarbon fluid, either by analysing a fluid sample in a laboratory, or by carrying out in situ analysis of downhole fluids.

One problem faced in attempting to measure DP and BP temperature and/or pressures is finding an effective way of detecting the precise onset of the phase change in the fluid to be tested which occurs at the DP or BP i.e. detecting a DP or BP phase transition. Previously, the most common method of measuring BP pressure involved containing a representative two-phase (liquid and gas) sample of a fluid to be tested within a high pressure vessel and reducing the confining volume stepwise by injecting measured amounts of mercury into the vessel and recording the pressure at each volume, after shaking the vessel (to achieve equilibrium). Alternatively, a high pressure piston vessel is used to contain the sample and the piston is used to reduce the volume therein. By plotting measurements of volume against pressure, the point at which the fluid in the vessel changes from two phases (gas and liquid) to one phase (liquid) is detected as a marked change in the slope of the graph of pressure versus volume (due to a significant change in the compressibility of the pressure vessel contents at the BP). The pressure at which the slope changes is taken to be the bubble point pressure for the particular temperature of the vessel contents. However, where the fluid being tested is very volatile this change in slope may not be so marked and may be difficult to identify.

The most common methods of measuring DP pressures have involved visual identification of droplets of liquid formed at the DP. For fluids which exhibit what is commonly known as "retrograde condensation" behaviour, a fluid sample is contained within a high pressure vessel and is compressed to a point where it is a single, gaseous phase. The pressure in the vessel is then reduced stepwise, with the vessel being shaken after each volume reduction (to achieve equilibrium).

When the fluid reaches the DP pressure (for the particular temperature of the vessel contents), droplets of liquid can be observed coming out of the fluid and accumulating at the lowest point in the cell, and for some fluids a colour change will also be observed as the fluid approaches the dew point. For fluids which exhibit more "conventional" condensation behaviour, the process is modified in that the vessel is filled with a single, gaseous phase, sample of the fluid at low pressure and the pressure is then increased stepwise until droplets of liquid are observed. Such visual identification is error prone and often produces inaccurate measurements of dew point pressures.

It is an aim of the present invention to substantially avoid or minimise one or more of the foregoing disadvantages.

According to a first aspect of the invention we provide apparatus for detecting a dew point or bubble point phase transition in fluid, the apparatus comprising: a piezoelectric crystal sensor formed and arranged to resonate at a variable frequency which is dependent upon physical properties of fluid in contact with the sensor; and signal analyser means formed and arranged for monitoring, in use of the apparatus, directly or indirectly, change in the resonant frequency of the piezoelectric crystal sensor while one of the temperature and pressure of a sample of fluid in contact with said sensor is varied, so as to detect a substantial change in said resonant frequency and/or in the rate of change in resonant frequency with change in the varying one of the temperature and pressure, occurring at a dew or bubble point phase transition of the sample of fluid, whereby a said dew or bubble point phase transition may be detected.

An advantage of the apparatus according to the invention is that it enables highly accurate detection of the dew point, or bubble point, phase transition in a fluid to be achieved. The detection of the DP or BP does not require any visual identification of the formation of droplets of liquid, or bubbles of gas, often used in other methods for detecting DP, or BP, and which can lead to problems and errors in the detection and subsequent calculation of the DP or BP. Moreover, only a relatively small amount of fluid is required i.e. a sufficient amount of fluid to contact, preferably to surround, the piezoelectric crystal sensor which may be very small e.g. of the order of 10 mm diameter, is required. Other advantages include extreme versatility of the sensor: the sensor may be is used at all, or at least most, temperatures and pressures likely to be encountered when measuring dew or bubble point temperature/pressure measurements on oil field reservoirs. The piezoelectric crystal sensor incorporated in the apparatus is also relatively inexpensive in comparison with some other sensors incorporated in the prior known types of apparatus.

For the avoidance of doubt, the dew point (DP) phase transition is defined herein as the appearance of a liquid phase (e.g. droplets) in a gas, and the bubble point (BP) phase transition as the appearance of a gaseous phase (e.g. bubbles) in a liquid. It will be understood that at the DP or BP phase transition the single phase fluid may become (at least temporarily) a two phase fluid (i.e. a gas/liquid mixture).

The apparatus preferably also includes at least one of temperature measuring means and pressure measuring means formed and arranged for measuring those of the temperature and pressure of the sample fluid in contact with the piezoelectric crystal sensor which are varied in use of the apparatus.

Preferably, the piezoelectric crystal sensor is an acoustic wave sensor selected from the group consisting of thickness-shear-mode (TSM) devices, surface-acoustic-wave (SAW) devices, acoustic-plate-mode (APM) devices and flexural-plate-wave (FPW) devices.

The piezoelectric crystal sensor preferably comprises a quartz crystal microbalance (QCM). The QCM conveniently comprises an AT-cut quartz crystal sandwiched between excitation electrodes to which a driving signal may be applied to generate a transverse shear wave across the thickness of the crystal. Such a QCM can be made to oscillate even when immersed in fluid (gas or liquid) and will resonate at a frequency which is related to properties such as the density and viscosity of the surrounding fluid. Any change of phase in the fluid will significantly change the resonant frequency of the QCM, and/or the rate of change in resonant frequency of the QCM with change in temperature or change in pressure.

The signal analyser means is preferably adapted to control the driving signal supplied to the excitation electrodes and may be adapted to, for example, analyse the phase of an electrical impedance or gain of the sensor so as to detect a resonant condition of the sensor (occurring at a resonant frequency of the sensor). Similarly, the resonant condition could be detected by monitoring, for example, current, voltage or electrical conductance of the sensor so as to detect a resonant condition thereof. In use of the apparatus, the signal analyser means is advantageously adapted to produce and detect a resonant condition of the sensor at a predetermined number of different pressures, or temperatures, of the fluid in contact with the sensor.

The analyser means is preferably adapted to measure, and conveniently also to store or record, the value of the (driving) signal frequency, and/or one or more of the sensor current, voltage and conductance, at each detected resonant condition of the sensor. Change in the resonant frequency may thus be monitored directly, or alternatively indirectly by monitoring change in the values of, for example, current, voltage or conductance, at resonant frequency.

At the DP or BP phase transition there may be a quantum change in the resonant frequency which may be, for example, a few hundred to a few thousand Hertz. Additionally, or alternatively, there may be a substantial change in the rate of change of resonant frequency with the changing temperature, or the changing pressure. This latter change can be seen clearly as a significant change in the slope of a graph of resonant frequency versus temperature or pressure respectively. This change in slope may, for example, be a change from a negative to a positive slope, or vice versa.

Where the piezoelectric crystal sensor comprises a QCM, the quartz crystal incorporated therein is preferably a polished crystal. This has the advantage of minimising any interference which may occur in use of the QCM caused by molecules trapped on the surface of the quartz crystal.

Advantageously, the apparatus further includes a pressure vessel comprising a pressure chamber in which the piezoelectric crystal sensor is mounted. In use of the apparatus, a sample of fluid to be analysed is injected or otherwise inserted into the pressure chamber so as to surround the piezoelectric crystal sensor. Preferably, the apparatus includes pressure control means formed and arranged for varying the pressure of fluid in the pressure chamber. The pressure control means may conveniently comprise a piston and the pressure chamber of the pressure vessel may comprise a piston cell in which the piston is arranged for sliding movement therein. Alternatively, the pressure control means may comprise pump means for compressing or evacuating fluid in/from the pressure chamber. Where pump means is provided, valve control means is preferably provided for controlling the flow of fluid into and out of the chamber.

The apparatus of the invention preferably includes temperature control means formed and arranged for varying the temperature of the fluid in the pressure chamber. The temperature control means may conveniently be provided in the form of a heating jacket surrounding the pressure vessel. Electrical power may be supplied to the heating jacket so as to raise and maintain the temperature of the fluid sample int he pressure vessel above room temperature, where desired. Additionally, or alternatively, the temperature control means may include cooling means, for example, a heat sink.

The apparatus conveniently includes a pressure vessel mounting means incorporating a pivotal mounting for the pressure vessel, whereby the pressure vessel is pivotally mounted to allow rotation of the vessel, in use of the apparatus, so as to mix the fluid contents of the vessel.

According to another aspect of the invention we provide a method of detecting a dew point or bubble point phase transition in a fluid, the method comprising the steps of:

a) providing a piezoelectric crystal sensor which is formed and arranged to resonate at a variable frequency which is dependent upon physical properties of any fluid in contact therewith;

b) immersing at least one surface of the sensor in a sample of a fluid to be tested, so that said sensor surface is in contact with said fluid;

c) varying one of the temperature and pressure of the fluid sample so as to cause a dew point or bubble point phase transition to occur in the fluid, while maintaining the other one of the temperature and pressure substantially constant; and d) monitoring, directly or indirectly, change in the resonant frequency of the piezoelectric crystal sensor while said one of the temperature and pressure is varied, so as to detect a substantial change in said resonant frequency and/or in the rate of change in resonant frequency with change in the varying one of the temperature and pressure, which occurs at the dew point or bubble point phase transition in the fluid, thereby to detect a said dew point or bubble point phase transition.

This method has the advantage of avoiding the need for any exact and/or accurate measurement of any nominated electrical property, relying only on direct or indirect detection of a substantial change in the resonant frequency of the sensor, or rate of change of resonant frequency of the sensor with change in temperature, or change in pressure, in order to identify the dew point or bubble point phase transition.

The detection of said substantial change in resonant frequency and/or rate of change of resonant frequency may be achieved by recording monitored values of resonant frequency, or for example, current, voltage or conductance at resonant frequency, and the corresponding varying temperature or pressure values, for example in graphical form, thereby recording the substantial change in the resonant frequency (or rate of change in resonant frequency), or the nominated other electrical property at resonant frequency, occurring at the dew point or bubble point phase transition in the fluid.

The method preferably further includes measuring the magnitude of the varying one of the temperature and pressure when said significant change in resonant frequency and/or rate of change in resonant frequency occurs, and the magnitude of the other one of the temperature and pressure which is held substantially constant. These measurements provide the dew or bubble point temperature of the sample fluid at a given pressure, or alternatively the dew of bubble point pressure of the sample fluid at a given temperature. Conveniently, the temperature and pressure of the sample fluid is continuously measured while said one of the temperature and pressure is varied.

Where the sample fluid is a gas, or a mixture of conventional gases, which exhibit(s) retrograde condensation behaviour, the method may comprise increasing the pressure of the fluid well above the dew point pressure and then gradually decreasing the pressure of the fluid while maintaining the temperature constant, so as to cause drops of liquid to condense out of the gaseous fluid, and monitoring the resonant frequency, of the sensor at various pressures above and below, the pressure at which the onset of the gas to liquid phase transition occurs, the pressure being the dew point (DP) pressure for the sample fluid at the particular temperature of the sample fluid. Advantageously, the pressure of the sample fluid is continuously measure so that the magnitude of the pressure at the dew point may be obtained by, for example, analysing a graph of pressure against resonant frequency, or pressure against conductance at resonant frequency.

In a similar manner, bubble point temperatures and pressures can be detected and/or measured using the above-described methods where the sample of fluid is a liquid, by measuring the temperature and pressure at which the onset of the liquid to gas phase transition (ie, the formation of bubbles of gas) occurs.

The apparatus and/or method as above-described may be used in various possible applications. For example, the apparatus may be used in a laboratory for detecting and measuring dew point and/bubble point temperatures of fluids. The apparatus may alternatively be used for in situ monitoring of fluids in downhole applications. In such applications, the apparatus may be used for detecting and measuring dew point or bubble point temperatures, and/or pressures. The apparatus could alternatively be used in safety applications where, for example, the apparatus may be mounted in an underground pipe or bore for detecting a DP or BP phase transition, signifying a change in environmental and/or safety conditions. In this latter application the apparatus may conveniently further comprise visible or audible warning indicator means, such as an alarm, for indicating when a dew point of bubble point phase transition has been detected.

Preferred embodiments of the invention will now be described, by way of example only, and with reference to the accompanying drawings in which.

Figure 1A:
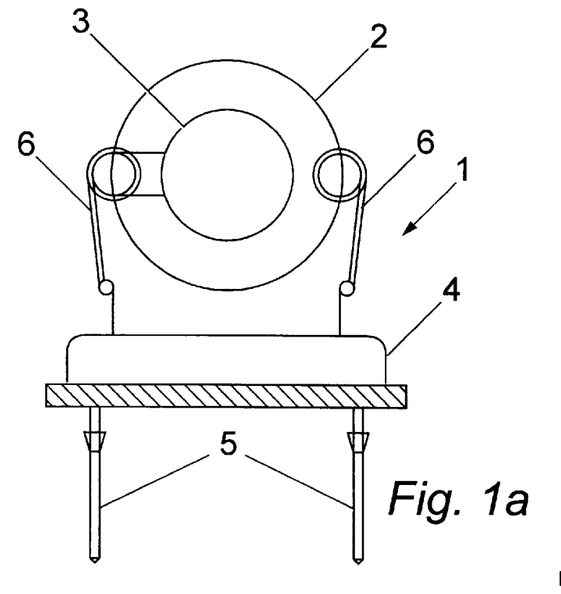
FIG. 1(a) is a schematic side view (enlarged) of a quartz crystal microbalance (QCM)
Figure 1B:
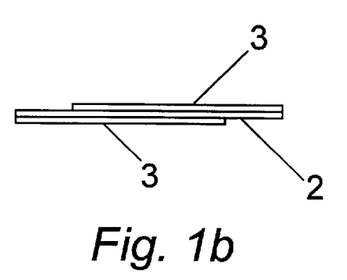
FIG. 1(b) is an end view of the arrangement of the quartz crystal and the electrodes of the QCM of FIG. 1(a)

FIG. 1(a) shows schematically a typical Quartz Crystal Microbalance (QCM) 1. The QCM comprises an AT-cut polished quartz crystal 2 sandwiched between two gold excitation electrodes 3 (as shown in detail in FIG. 1(b)) that generate a transverse shear wave across the thickness of the quartz crystal (when a driving electrical signal is applied to the electrodes). The crystal 2 has an inherent resonant frequency at 5 MHz. The crystal 2 is mounted, by means of two connecting wires 6 connected to respective ones of the electrodes 3, to a mounting base 4, as shown. Driving signals are applied to the connecting wires 6 via conducting pins 5 which extend through the mounting base 4.

Although FIG. 1 shows a transverse shear wave device, it is to be understood that the apparatus of the invention may use other piezoelectric acoustic-wave devices such as surface-acoustic-wave (SAW), acoustic-plate-mode (APM) and flexural-plate-wave (FPW) devices.

Figure 2:
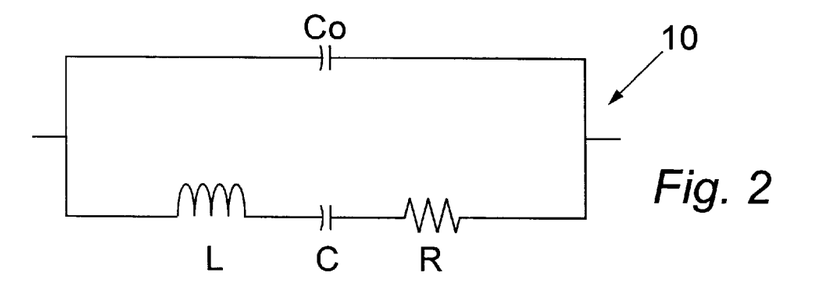
FIG. 2 is a schematic diagram of the equivalent electrical circuit representing the electrical behaviour of the QCM.

FIG. 2 shows the elements of an equivalent electrical circuit 10 which the resonant electrical behaviour of the QCM imitates. As shown, the equivalent electrical circuit 10 comprises a resistor R, capacitor C and inductor L, all in series, which are in parallel with an additional capacitance Co defined as the static capacitance of the quartz crystal.

Figure 3:
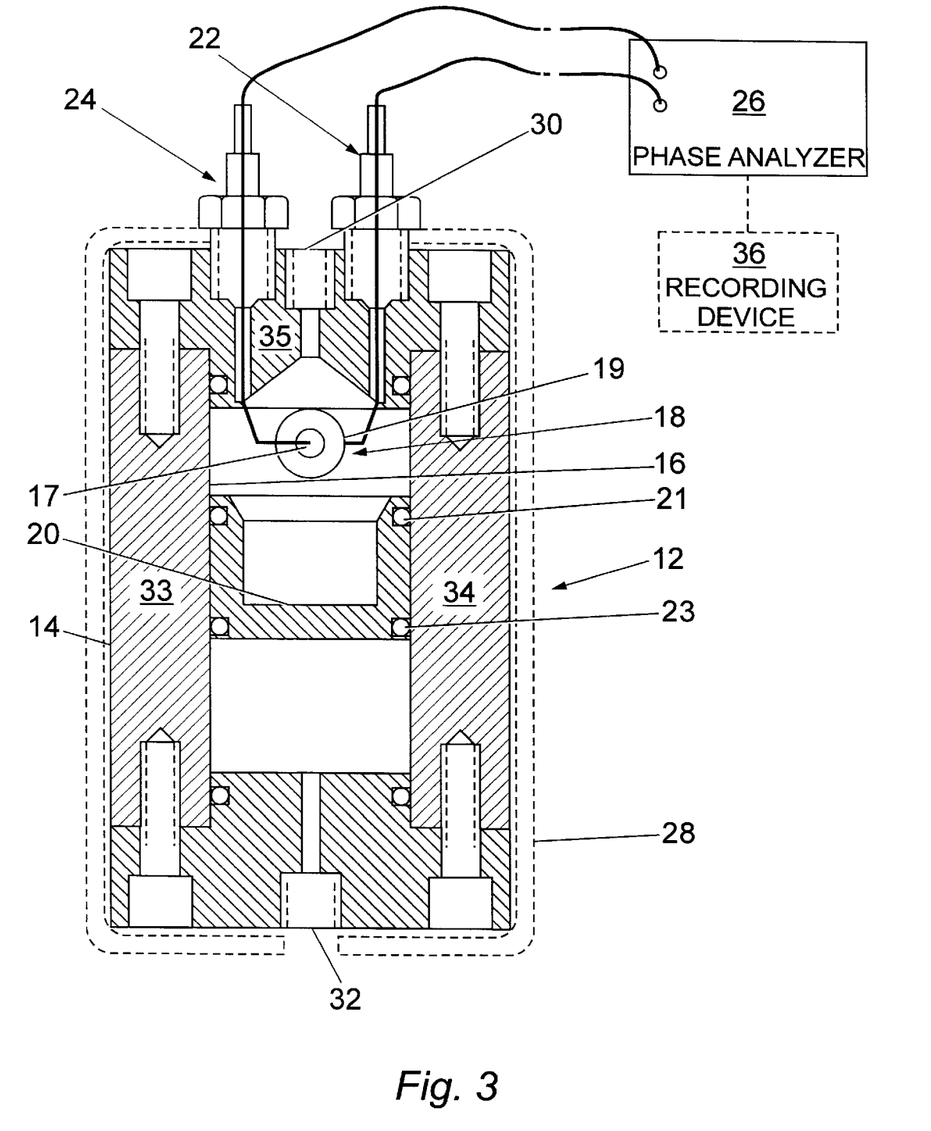
FIG. 3 is a cross-sectional side view of an apparatus according to the invention for detecting the dew point (DP) or bubble point (BP) of a fluid.

FIG. 3 shows a cross-section through a dew point of bubble point detection apparatus 12 according to a preferred embodiment of the invention. The apparatus 12 comprises a stainless steel piston vessel 14 having an internal, generally cylindrical, piston chamber 16 of volume 180 cc (cubic centimetres) having a piston 20 located for sliding movement therein. Two ring seals 21, 23 mounted on the piston 20 make sealing contact between the piston and the wall of the chamber 16. A QCM 18 is mounted in the piston vessel 12, in the piston chamber 16, towards one end thereof. The two electrodes 17 (only one shown) of the QCM are gold, are bonded to the surfaces of the QCM crystal 19, and are connected, via respective high pressure electric feed through 22, 24 built into the piston vessel 14, to an HP4194A impedance/gain phase analyser 26 (indicated in block form only) located remote from the piston vessel 14. The piston vessel 14 is mounted on a pivot (not shown) to allow for rotation of the vessel, and thus mixing of contents of the vessel. The piston vessel 14 is also surrounded by a heating jacket 28 (indicated in broken lines) for controlling the temperature of contents of the vessel 14.

In use of the apparatus, the piston chamber 16 is charged with a single phase (gas or liquid) test fluid to be analysed. The test fluid is introduced into the chamber 16 via a sample inlet port 30 provided in the piston vessel 14, to fill a portion of the piston chamber defined between the piston 20 and three walls 33, 34, 35 of the piston chamber 16, the QCM consequently being immersed in the test fluid. The pressure in the piston chamber 16 is controllable by moving the piston 20 so as to change the volume of the portion of the piston chamber 16 in which the test fluid is contained. Movement of the piston 20 is controlled by external pressure control means, for example, a pump (not shown) which is connected to the piston chamber 16 via a pressure port 32 provided in the piston vessel 14. A temperature sensor (not shown) of the platinum resistance probe type is provided in the apparatus, in the heating jacket 28, for continuously monitoring the temperature of the heating jacket (which is substantially the same, or closely approximates to, the temperature in the piston chamber). A pressure sensor (not shown) in the form of a strain gauge transducer is located in a branch off the sample inlet port 30 of the pressure vessel and is arranged to continuously monitor the pressure therein.

In order to detect and measure a dew point or bubble point phase transition in the fluid sample to be tested, either the piston chamber temperature is kept constant and the pressure is varied stepwise (so as to enable a dew or bubble point pressure at a given temperature to be measured), or the pressure is kept constant and the temperature is varied stepwise (so as to measure the dew or bubble point of the fluid at a given pressure). At each temperature and pressure equilibrium is achieved in the piston chamber by rotating the piston vessel 14 on its pivot so as to mix the contents of the piston chamber 16. Once equilibrium has been reached, measurements of resonant frequency, and conductance at resonant frequency $C_R$, of the QCM are taken using the phase analyser 26.

Figure 4:
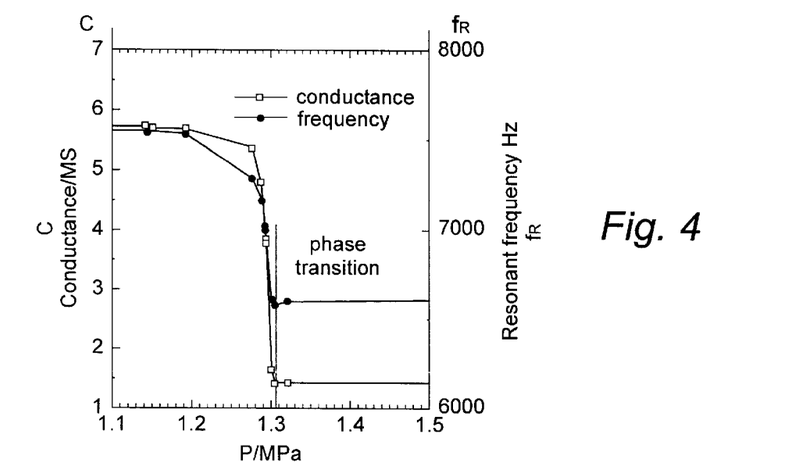
FIG. 4 shows graphs of resonant frequency vs. pressure, and conductance at resonant frequency vs. pressure, obtained using the apparatus of FIG. 3, illustrating a phase change occurring at the BP in liquid propane, at 311K.
Figure 5:
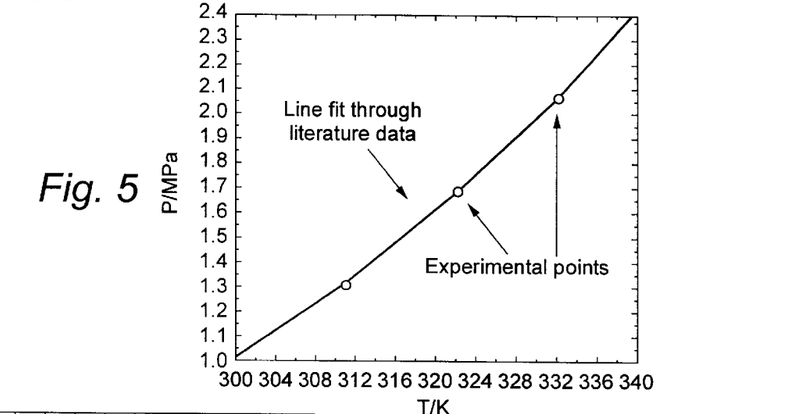
FIG. 5 is a graph of pressure vs. temperature at the phase boundary in liquid propane, comparing theoretical data with experimental data obtained using apparatus according to the invention.

In a first experimental example, FIG. 4 illustrates graphically the detection of the bubble point pressure in propane at 311K. In this experiment, the temperature was kept constant while the pressure was varied in a step-like manner. At each pressure the resonant frequency and the Conductance at resonant frequency of the QCM was measured by the phase analyser 26 and recorded by a recording device 36 connected hereto (eg. a printer, or a microprocessor with a VDU). By plotting a graph of resonant frequency $f_R$ against a pressure P, and/or a graph of Conductance $C_R$ at resonant frequency against pressure P, the BP phase transition can be seen clearly in the graph as a significant change in the resonant frequency $f_R$ (of approx. 1300 Hz), or in Conductance at resonant frequency $C_R$ (changing by approx. 4 MS), occurring at the bubble point (BP) pressure (approx. 1.31 MPa). FIG. 5 is a graph of pressure P vs. temperature T plotted using theoretically calculated values for propane in the region if the liquid/gas phase boundary. Experimental points obtained from the experimental data collected with the apparatus of the invention are indicated on the graph in FIG. 5 and it can be seen that there is a good agreement between the theoretical and experimental data.

Figure 6:
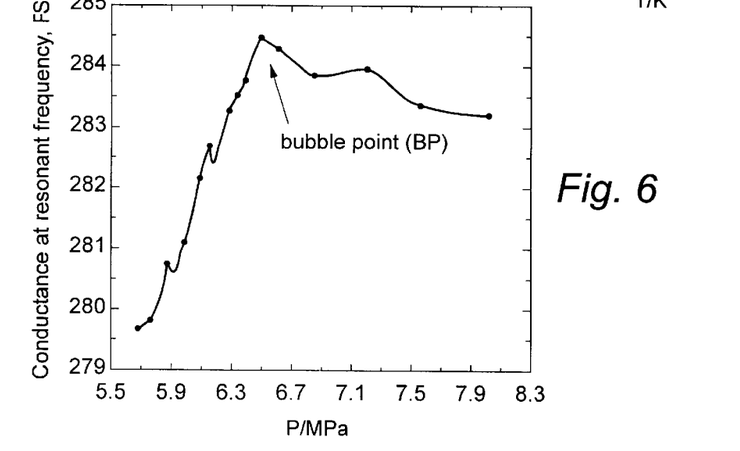
FIG. 6 is a graph of conductance at resonant frequency vs. pressure, obtaining using the apparatus of FIG. 3, illustrating a phase change occurring at the BP in black oil, at 294K.

FIG. 6 illustrates another example, in which the apparatus of FIG. 3 was used to measure the bubble point pressure for black oil at 294K. From the graph of Conductance at resonant frequency, $C_R$, vs. pressure, P, it can be seen that the gas phase appeared at a BP pressure of approx. 6.5 MPa at which pressure the slope of the graph changes significantly (from positive to negative, as the pressure increases).

Figure 7:
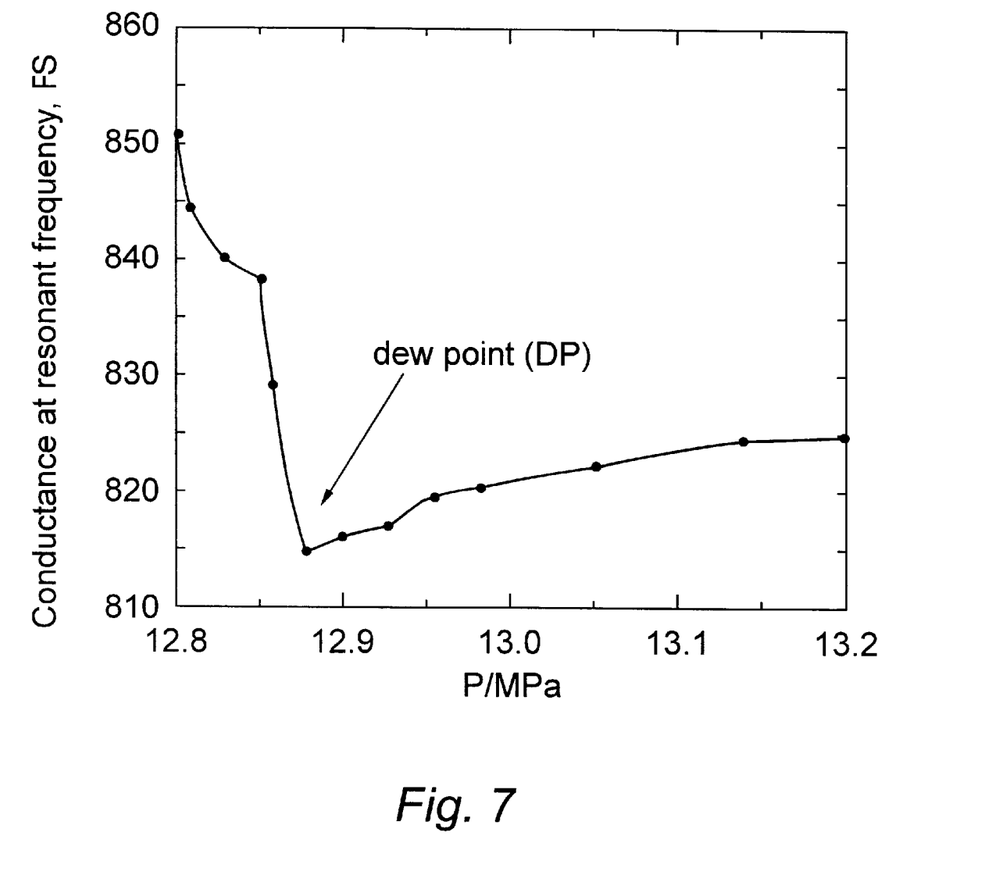
FIG. 7 is a graph of conductance at resonant frequency vs. pressure, obtained using the apparatus of FIG. 3, illustrating a phase change occurring at the DP in a binary mix of methane/butane, at 311K.

FIG. 7 illustrates a further example, in which the dew point (DP) pressure of a binary mix of methane and butane composed of 74 mole % methane was measured, at a constant temperature of 311K. The mix of methane and butane exhibits retrograde condensation behaviour. In order to detect the dew point, the pressure in the chamber 16 was increased by volume reduction to well above the dew point pressure. The pressure was then decreased stepwise and the Conductance at resonant frequency recorded at each step. A shown in FIG. 7, a significant change in the slope of the graph of Conductance at resonant frequency, $C_R$, vs. pressure, P, occurred at the DP pressure (approx. 12.87 Mpa). In fact, the slope of the graph changes from positive to negative (with decreasing pressure), at the DP pressure.

Figure 8:
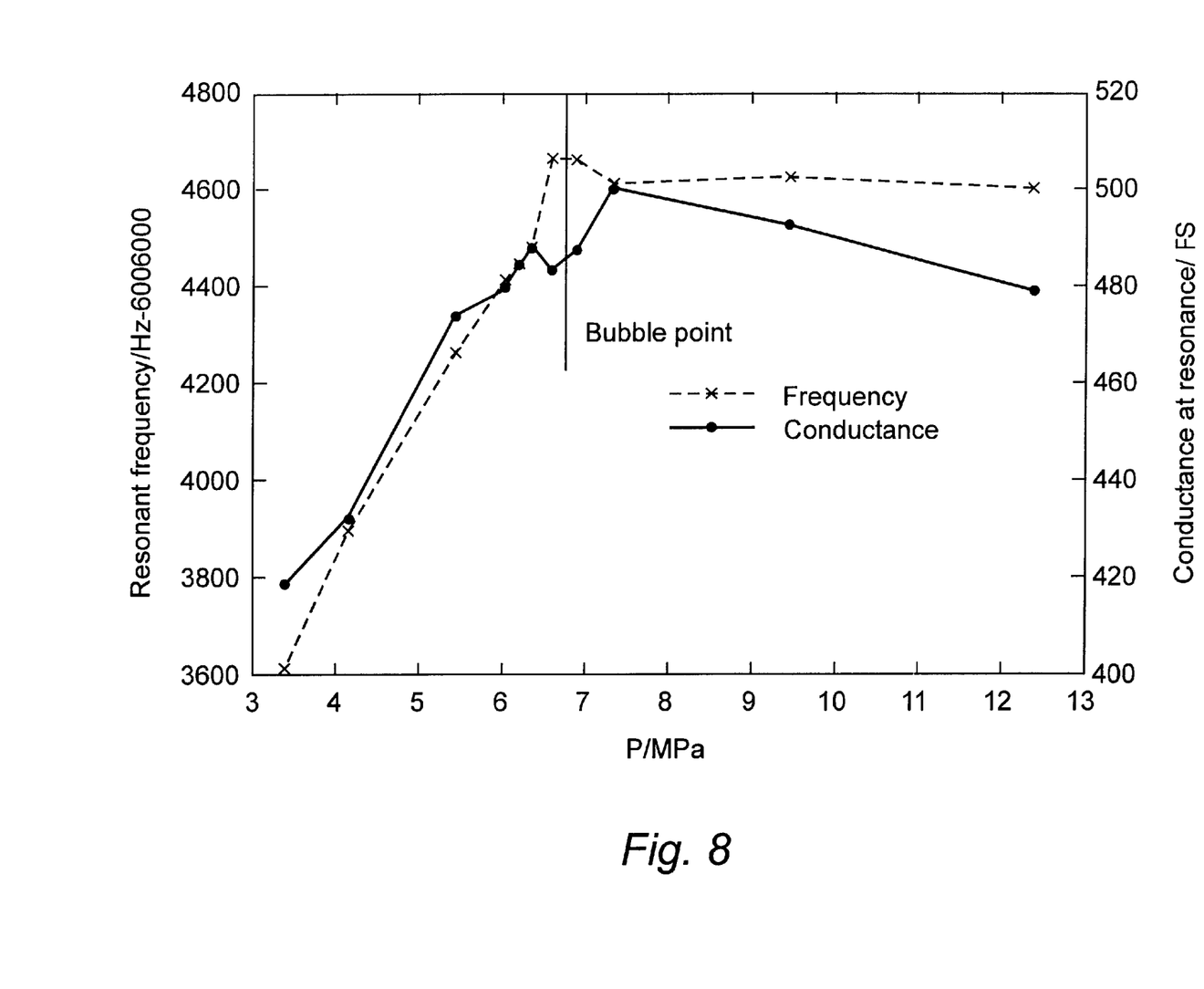
FIG. 8 is a graph of conductance at resonant frequency vs. pressure, obtained using the apparatus of FIG. 3, illustrating a phase change occurring at the BP in black oil containing contaminants.

In the method of the invention it has been shown that the measurements can be made in the presence of contamination in the form of sand particles and drilling mud. The reason for this is that the contamination will only interfere with measurements if it actually adheres to the quartz crystal. It has also been shown that measurement can be made with a water cut present so long as the water phase does not become continuous and remains as an emulsion with the oil. This strengthens the potential for the device to be used in a downhole tool. FIG. 8 shows the results of a bubble point determination with contamination present.

It is believed that the accuracy achieved in the measurement of DP and BP pressures obtained with the apparatus of FIG. 3 is a least as good as the accuracy achieved with previously known types of DP or BP measurement equipment. Due to the relatively small size of measurement samples needed and the fact that the apparatus does not rely on visual identification techniques, the apparatus of FIG. 3 is moreover more convenient and simpler to use then the previously known apparatus. (Ultimately, the accuracy will be limited by the quality of the temperature and pressure sensors used).

It will be appreciated that various modifications to the invention are possible without departing from the scope of the invention. For example, while the apparatus described in relation to FIG. 3 is essentially for use on a laboratory environment, the apparatus may be adapted to use in field applications, for example in downhole applications. In such applications, the apparatus may in its simplest form comprise a QCM sensor connected to a phase analyser. The QCM is lowered down the bore or pipe, in use, and the phase analyser is operated remotely (outside or above the bore or pipe) to obtain the necessary measurements on fluid present in the bore/pipe. Pressure of fluid in the bore/pipe being analysed maya be controlled using natural pressure build ups and pressure release obtained when a lid or valved opening to the bore or pipe is opened/closed. The temperature of fluid in the bore/pipe will, in most cases, be substantially constant. For such applications it may be necessary to provide the QCM sensor with an anti-contamination shield to prevent loose particles and other debris present downhole from contaminating the surface(s) of the sensor.

In other possible embodiments, the apparatus may be used for safety applications in order to detect, rather than measure, the dew or bubble point phase transition occurring in a fluid, or fluid mixture, in for example a bore or pipe. A warning alarm and/or flashing light may be connected to the phase analyser or recorder means, the latter being adapted to activate the alarm/flashing light when a phase transition is detected.

What is claimed is:

1. A phase transition detection apparatus for detecting the dew point and bubble point phase transition in a fluid, the apparatus comprising:

a pressure chamber for holding said fluid;

a piezoelectric crystal sensor mounted in said pressure chamber and in contact with said fluid, said crystal sensor being formed and arranged to resonate at a variable resonant frequency which is dependent upon physical properties of the fluid in contact with the crystal sensor; and means for directly or indirectly monitoring, in use of the apparatus, changes in the resonant frequency of the piezoelectric crystal sensor consequent upon variations of one of the temperature and pressure of said fluid in contact with said sensor, whereby to detect a substantial change in said resonant frequency and/or a substantial change in the rate of change with respect to time of said resonant frequency consequent upon variations of the varying one of the temperature and pressure, said substantial change occurring at the dew or bubble point phase transition of the fluid, whereby the said dew or bubble point phase transition may be detected;

the pressure chamber being adapted to hold a sufficient amount of said fluid to contact or surround the piezoelectric crystal sensor; and means for controllably varying the pressure and/or temperature of said fluid in the pressure chamber.

2. The apparatus according to claim 1, wherein the means for controllably varying the pressure and/or temperature comprises means for varying the pressure of fluid in the pressure chamber.

3. The apparatus according to claim 2, wherein the means for varying the pressure comprises a piston, and the pressure chamber comprises a piston cell having an internal bore therein, in which the piston is arranged for sliding movement therethrough.

4. The apparatus according to claim 2, wherein the means for varying the pressure comprises means for compressing or evacuating fluid in or from the pressure chamber.

5. The apparatus according to claim 4, wherein the means for compressing or evacuating fluid in or from the pressure chamber comprises means for controlling the flow of fluid into and out of the pressure chamber.

6. The apparatus according to claim 1, wherein the means for controllably varying the pressure and/or temperature is means for varying the temperature of the fluid in the pressure chamber.

7. The apparatus according to claim 6, wherein said means for varying the temperature of the fluid comprises a heating jacket surrounding the fluid chamber.

8. The apparatus according to claim 6, wherein the means for varying the temperature of the fluid includes means for cooling.

9. The apparatus according to claim 8, wherein the means for cooling is a heat sink.

10. The apparatus according to claim 1, wherein the piezoelectric crystal sensor is substantially planar and has a diameter of less than 30 mm, and the chamber has an internal dimension measured in the plane of the sensor less than 3 times the diameter of the sensor.

11. The apparatus according to claim 1, further comprising at least one of means for measuring temperature and means for measuring presure of the fluid in contact with the piezoelectric crystal sensor which are varied in use of the apparatus.

12. The apparatus according to claim 1, wherein the piezoelectric crystal sensor is an acoustic wave sensor selected from the group consisting of thickness-shear-mode (TSM) devices, surface-acoustic-wave (SAW) devices, acoustic-plate-mode (APM) devices and flexural-plate-wave (FPW) devices.

13. The apparatus according to claim 12, wherein the piezoelectric crystal sensor is a quartz crystal microbalance comprising an AT-cut quartz crystal sandwiched between a pair of excitation electrodes to which a driving signal may be applied to generate a transverse shear wave across the thickness of the crystal.

14. The apparatus according to claim 13, wherein the means for directly or indirectly monitoring in use of the apparatus, changes in the resonant frequency of the piezoelectric crystal sensor controls the driving signal supplied to the excitation electrodes.

15. The apparatus according to claims 13 or 14, wherein the means for directly or indirectly monitoring in use of the apparatus, changes in the resonant frequency of the piezoelectric crystal sensor analyzes the phase of an electrical impedance or gain of the sensor so as to detect a resonant condition of the sensor which occurs at a resonant frequency of the sensor.

16. The apparatus according to claim 15, wherein the resonant condition is detected by monitoring current, voltage or electrical conductance of the sensor.

17. The apparatus according to claim 1, wherein the means for directly or indirectly monitoring in use of the apparatus, changes in the resonant frequency of the piezoelectric crystal sensor comprises means for producing and detecting a resonant condition of the sensor at a predetermined number of different pressures, or temperatures, of the fluid in contact with the sensor.

18. The apparatus according to claim 1, wherein the means for directly or indirectly monitoring in use of the apparatus, changes in the resonant frequency of the piezoelectric crystal sensor comprises a driving signal generator and means for measuring the frequency of the driving signal and/or one or more of the sensor current, voltage and conductance, at each detected resonant condition of the sensor.

19. The apparatus according to claim 18, wherein the means for directly or indirectly monitoring in use of the apparatus, changes in the resonant frequency of the piezoelectric crystal sensor comprises means for monitoring the change in the resonant frequency.

20. The apparatus according to claim 19, wherein said means for monitoring the change in the resonant frequency monitors the change in the values of current, voltage or conductance, at resonant frequency.

21. The apparatus according to claim 18, wherein the means for directly or indirectly monitoring in use of the apparatus, changes in the resonant frequency of the piezoelectric crystal sensor comprises means for storing and/or recording the value of the driving signal frequency, and/or one or more of the sensor current, voltage and conductance, at each detected resonant condition of the sensor.

22. The apparatus according to claim 1, wherein the means for directly or indirectly monitoring in use of the apparatus, changes in the resonant frequency of the piezoelectric crystal sensor comprises means for computation which recognizes and calculates the point at which there is a discontinuity in the change of resonant frequency with changing temperature or changing pressure.

23. The apparatus according to claim 22, wherein the discontinuity is a step change in the resonant frequency or a substantial change in the rate of change of resonant frequency with changing temperature or changing pressure.

24. The apparatus according to claim 1, wherein the pressure chamber is pivotally mounted to allow rotation of the chamber, in use of the apparatus, so as to mix the fluid contents of the chamber.

25. A method for detecting a dew point or bubble point phase transition in a fluid, the method comprising the steps of:
   a) providing a pressure chamber for holding said fluid;
   b) providing a piezoelectric crystal sensor which is formed and arranged to resonate at a variable resonant frequency which is dependent upon physical properties of any fluid in contact therewith;
   c) placing a sample of fluid to be tested in said pressure chamber;
   d) immersing at least one surface of the sensor in the sample of a fluid in the pressure chamber, so that said sensor surface is in contact with said sample;
   e) varying one of the temperature and pressure of the fluid sample in said pressure chamber so as to cause a dew point or bubble point phase transition to occur in the fluid, while maintaining the other one of the temperature and pressure substantially constant; and
   f) directly or indirectly monitoring changes in the resonant frequency of the piezoelectric crystal sensor while said one of the temperature and pressure is varied, so as to detect a substantial change in said resonant frequency and/or a substantial change in the rate of change with respect to time of said resonant frequency consequent upon variations of the temperature and pressure, said substantial change occurring at the dew point or bubble point phase transition in the fluid, thereby to detect the said dew point or bubble point phase transition.

26. The method according to claim 25, in which the detection of said substantial change in resonant frequency and/or rate of change of resonant frequency is achieved by recording monitored values of said resonant frequency.

27. The method according to claim 25, in which the detection of said substantial change in resonant frequency and/or rate of change of resonant frequency is achieved by recording monitored values of an electrical parameter dependent upon said resonant frequency, said parameter being selected from the group comprising current, voltage or conductance.

28. The method according to claim 25, further comprising the step of measuring the magnitude of the varying one of the temperature and pressure when said significant change in resonant frequency and/or rate of change in resonant frequency occurs, and the magnitude of the other one of the temperature and pressure which is held substantially constant.

29. The method according to claim 25, wherein the pressure of the fluid is increased to a point above the dew point pressure and then is gradually decreased, while maintaining the temperature constant, so as to cause drops of liquid to condense out of the gaseous fluid, and monitoring the resonant frequency of the sensor at various pressures above and below the pressure at which the onset of the gas to liquid phase transition occurs, this pressure being the dew point (DP) pressure for the sample fluid at the particular temperature of the sample fluid.

30. The method according to claim 25, wherein the pressure of the fluid is decreased to a point below the bubble point pressure and then is gradually increased, while maintaining the temperature constant, so as to cause the formation of bubbles of gas from within the liquid fluid, and monitoring the resonant frequency of the sensor at various pressures above and below the pressure at which the onset of the liquid to gas phase transition occurs, this pressure being the bubble point (BP) pressure for the sample fluid at the particular temperature of the sample fluid.

* * * * *